United States Patent [19]

Nagabhushan et al.

[11] Patent Number: 4,751,078

[45] Date of Patent: Jun. 14, 1988

[54] PROCESS FOR THE PURIFICATION OF GAMMA INTERFERON

[76] Inventors: Tattanahalli L. Nagabhushan, 3 Sunset La., Parsippany, N.J. 07054; Paul P. Trotta, 405 Park Ave., Rutherford, N.J. 07070; Hung V. Le, 75 Valley View Dr., Rockaway, N.J. 07866; Gail F. Seelig, 130 Coriell Ave., Fanwood, N.J. 07023; Robert A. Kosecki, 29 White Birch La., Parsippany, N.J. 07054

[21] Appl. No.: 751,706

[22] Filed: Jul. 3, 1985

[51] Int. Cl.$^4$ .................... A61K 45/02; C07K 15/26; C12P 21/00
[52] U.S. Cl. ........................................ 424/85; 435/68; 435/811; 530/351

[58] Field of Search .......................... 530/351; 424/85; 435/68, 811, 172.3

[56] References Cited

U.S. PATENT DOCUMENTS 4,440,675  4/1984  Braude .................................. 424/85

*Primary Examiner*—Blondel Hazel
*Attorney, Agent, or Firm*—John J. Maitner; Stephen I. Miller; James R. Nelson

[57] ABSTRACT

A process is disclosed for purifying gamma interferon from various contaminants resulting from disruption of the cell in which the interferon was produced. The process provides for sequential removal of (a) nucleic acids, (b) negatively charged contaminating proteins, (c) positively charged contaminating proteins and (d) low and high molecular weight impurities.

16 Claims, 3 Drawing Sheets

PROCESS FOR THE PURIFICATION OF GAMMA INTERFERON

BACKGROUND

Interferon proteins have been classified into three types, alpha, beta and gamma based on antigenic and structural differences. Gamma interferon has a number of characteristics that differentiate it from alpha and beta interferons. Among these differences are antigenic distinctiveness and greater activity with regard to immunoregulation and antitumor effects. Human gamma interferon may be produced by T lymphocytes stimulated by mutagens or by antigens to which they are sensitized. It may also be obtained through cloning and expression techniques now well known to the art.

Gamma interferon containing cells, however obtained, are collected and are disrupted by various means such as osmotic shock, ultrasonic vibration, grinding or by high shear disruption. The disrupted cell-gamma interferon mixture is then processed to isolate the gamma interferon. The insoluble debris is separated by centrifugation and the gamma interferon containing supernatant is collected for purification. Several procedures are described in the art for separating and purifying gamma interferon from the supernatant collected from the centrifugation step.

European Patent Application No. 0,087,686 discloses a three step process for purifying human immune interferons from the cell free supernatant or extract from the crude interferon source. In the first step (for naturally occuring interferon), an affinity column, such as concanavalin-A Sepharose is used, followed by chromatography on a carboxymethyl silica column using an increasing salt gradient and finally, on a silica gel permeation column. If sufficient purity is not obtained, concentration and chromatography on either the TSK or CM column is used.

European Patent Application No. 0,063,482 discloses a purification process employing chromatographic methods using (1) Controlled Pore Glass (beads; 2) Concanavalin A-Sepharose; (3) Heparin-Sepharose or Procion Red-agarose; and (4) gel filtration.

European Patent Applications No. 0,107,498 and 0,077,670 disclose a purification scheme employing (1) polyethyleneimine precipitation; (2) pH precipitation of bacterial proteins; (3) concentration and dialysis; (4) chromatography on (a) carboxymethyl cellulose; (b) a calcium phosphate gel; (c) a carboxymethyl cellulose and (d) gel filtration resins.

These purification processes require a multitude of steps, have caused degradation of the interferon by degradation or aggregation of the interferon molecule, or otherwise result in a gamma interferon product obtained in low yield or with low activity.

It would be desirable to (1) provide a purification scheme to separate gamma interferon from the cell debris from the disrupted cells in which the gamma interferon was produced; (2) separate gamma interferon from cell contaminants in high yields and with high purity and activity; (3) separate recombinant gamma interferon from cell contaminants; and (4) separate gamma interferon from cell contaminants without substantially degrading the interferon. The purification process described below is such a process.

SUMMARY

The primary classes of contaminants in the disrupted cell/gamma interferon mixture are small size particulate matter and water soluble fractions such as nucleic acids, proteases, cell proteins, carbohydrates, lipids, cleaved interferon fragments and interferon aggregates and other fragments resulting from disruption of the cell in which the interferon was produced. We have now discovered that gamma interferon can be obtained in high purity, with the retention of biological activity and with good yields by processing the interferon-containing mixtures in a specific sequence as described below to minimize degradation of the interferon and to remove the contaminants from the interferon-containing mixture in a defined order.

Substantially improved purity and activity are obtained by removing the contaminants in the interferon-containing mixture in the following order:
 (1) nucleic acids;
 (2) negatively charged proteases and contaminating cell proteins;
 (3) positively charged proteases and contaminating cell proteins; and
 (4) cleaved and aggregated interferon.

This sequence of steps is critical to obtaining the desirable results of this invention. Provided that the listed contaminants are removed in the specified sequence, additional steps may be used to remove other comtaminating materials such as high molecular weight hydrophobic materials, if present. These other materials may conveniently be removed either after step 3 or after step 4.

There are numerous methods, known to the art, to accomplish each of these separations. As stated above, those methods which can accomplish the separations under the mildest conditions, to minimize degradation of the interferon, are the most desirable.

We have found that a preferred method is to use an initial polyethyleneimine precipitation followed by several chromatographic separations to remove the contaminants in the order specified above. The resins used in the chromatographic separations and the order of their use is as follows:
 (1) anion exchange resin;
 (2) cation exchange resin; and
 (3) molecular sieve.

In addition to the chromatographic separations, it is useful to employ precipitation, filtration, concentration and dialysis procedures.

In a preferred procedure the gamma interferon-containing mixture is subjected to the following procedures:
 (1) nucleic acid removal using polyethyleneimine precipitation;
 (2) negatively charged protease and contaminating cell protein removal using weakly basic anion exchange resin;
 (3) positively charged protease and contaminating cell protein removal using weakly acidic cation exchange resin; and
 (4) cleaved and aggregated interferon and cell fragment removal using a molecular sieve.

Filtration after each step, concentration after steps 3 and/or 4 and dialysis after step 5, are useful adjunctive procedures.

This novel procedure has consistently produced gamma interferon having a purity of at least 95% and a yield in excess of 5%.

Figure 1:
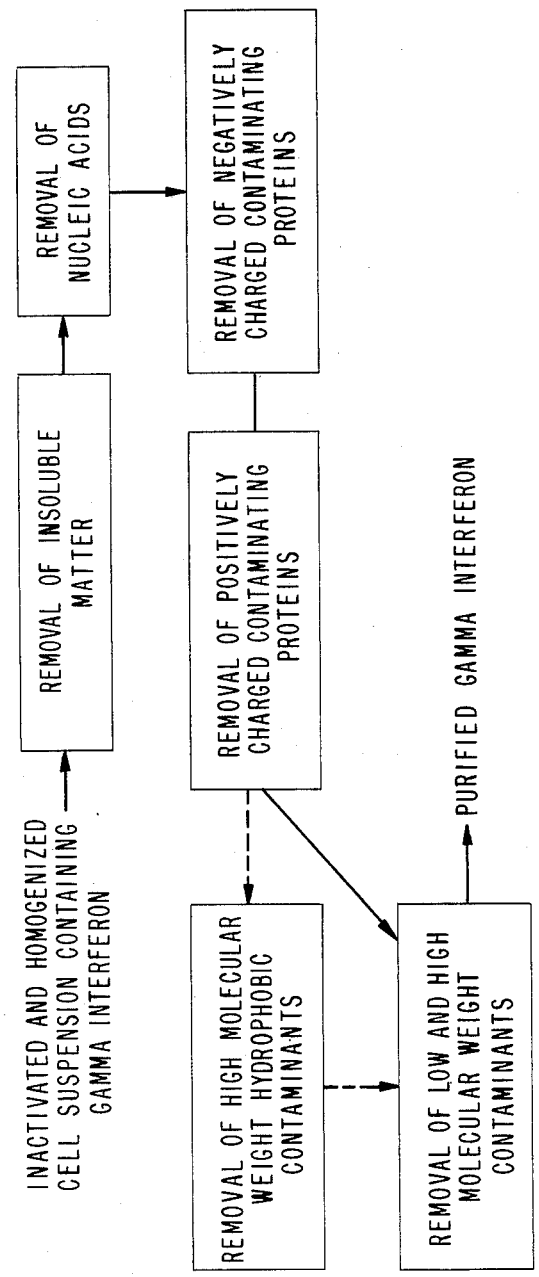
FIG. 1 is a flow diagram of the gamma interferon purification process of the present invention.
Figure 2:
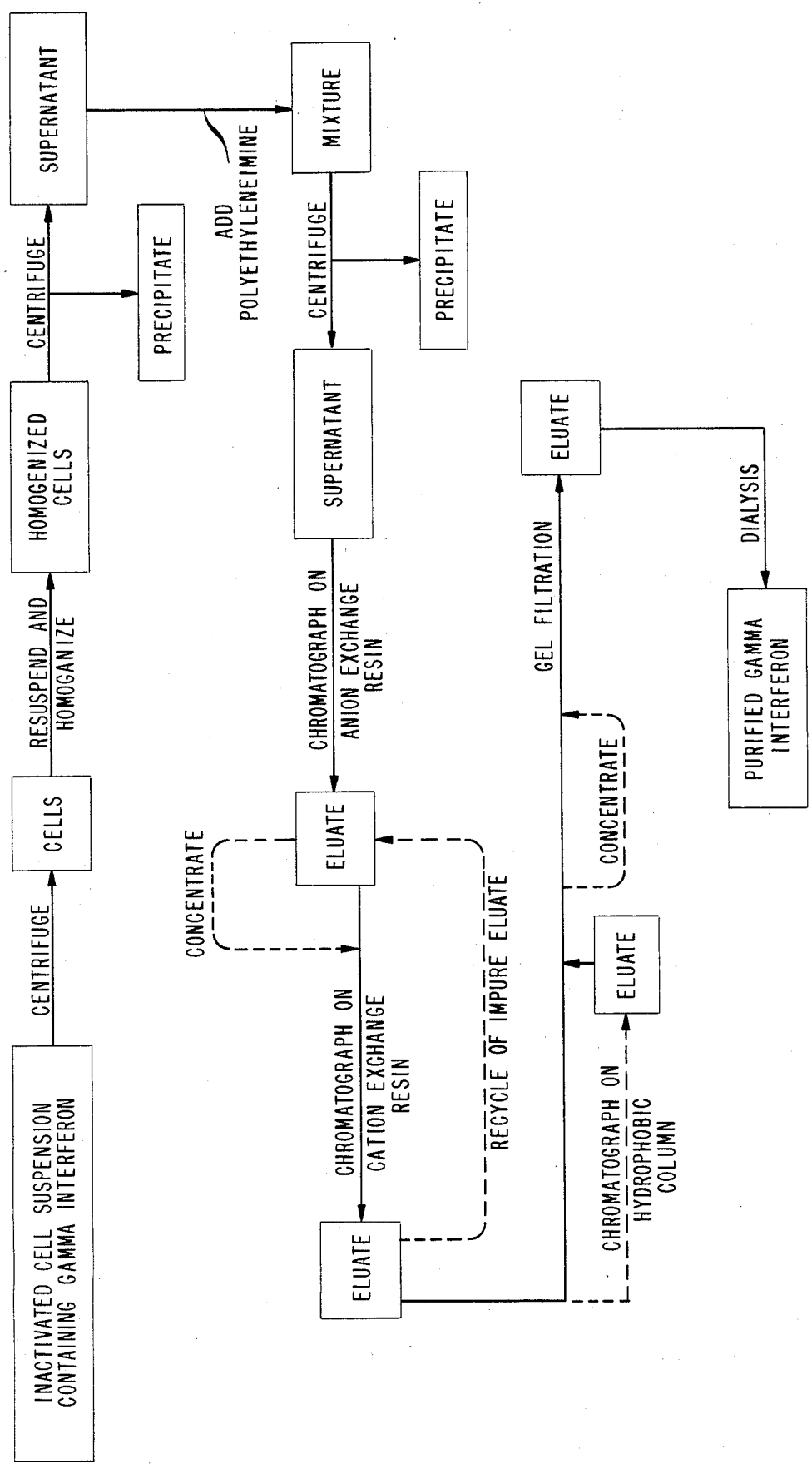
FIG. 2 is a flow diagram of the present invention showing the purification process using primarily chromatographic purification means.
Figure 3:
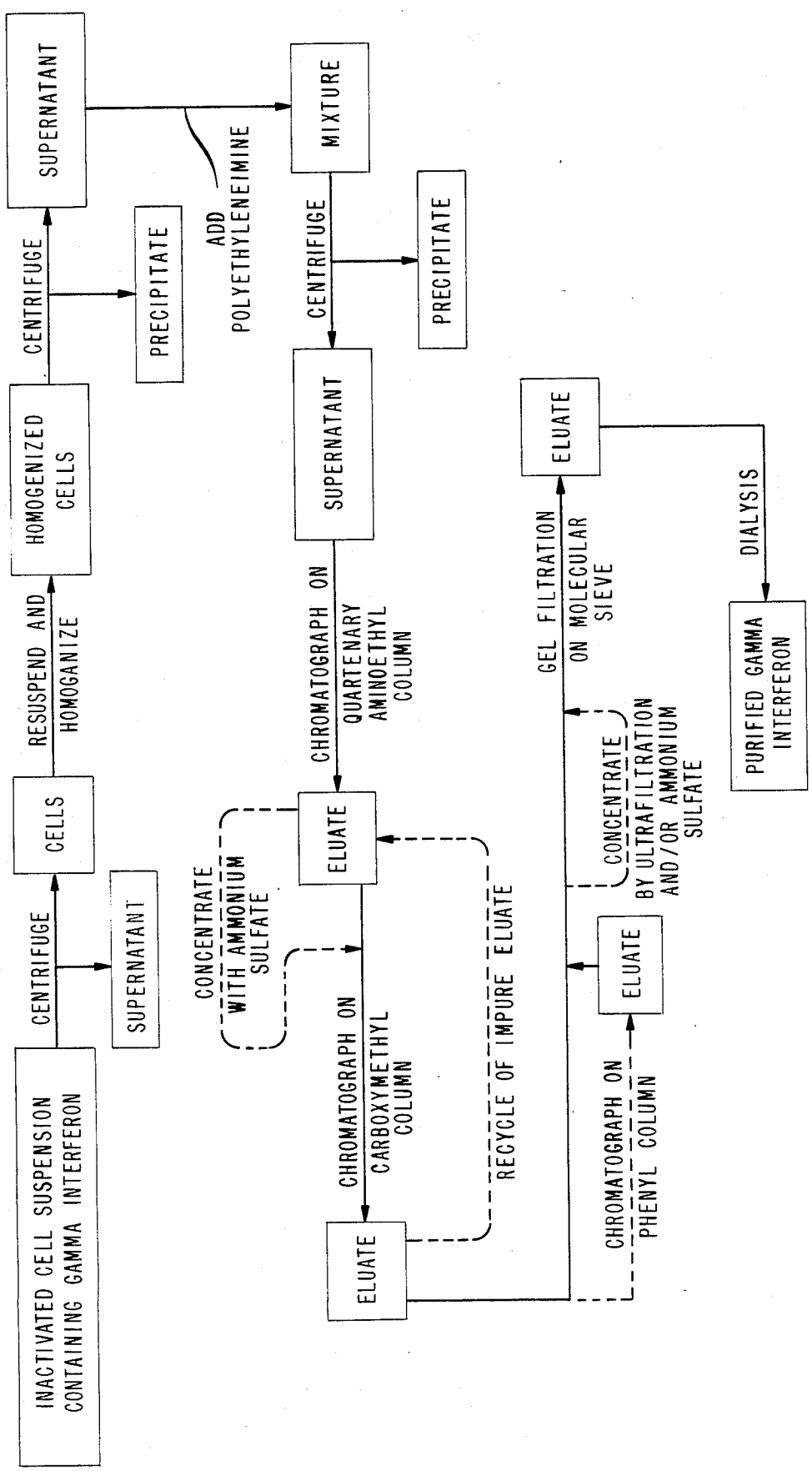
FIG. 3 is a flow diagram of a preferred embodiment of the present invention.

In all figures, the purification process starts with the removal of nucleic acids from the supernatant resulting from centrifugation of homogenized gamma interferon containing cells, prior steps being shown for clarity but not being part of the present invention.

DETAILED DESCRIPTION

The novel purification scheme which is the subject of the present invention is suitable for use with gamma interferon produced in any one of a number of ways such as from human cells grown in tissue culture, from leukocytes collected from blood samples or through cloning techniques well known in the art. The purification scheme is particularly well suited for the purification of recombinant gamma interferon recovered from *E. coli* cells. The cells are inactivated by one of the standard kill methods, such as by the addition of a chemical kill agent such as chlorhexidine gluconate. The inactivated cells are centrifuged, resuspended in a buffer and homogenized. A convenient method for homogenization of the gamma interferon-containing cells is by high shear disruption using a Manton-Gaulin homogenizer. The components of the disrupted cells are separated by centrifugation into a precipitate and supernatant. The supernatant from this process is a suitable source for gamma interferon to be isolated and purified by the method described herein.

The suspension of the lysed cells comprises proteins, lipids, carbohydrates and nucleic acids and insoluble cellular debris. Using conventional procedures, the water insoluble components are separated from the water soluble fraction of the cell which remains in the supernanant liquid.

It is sometimes desirable to provide certain preliminary processing steps prior to the extraction of the gamma interferon from the cells, such as procedures to minimize degradation of the interferon during processing. Any such preliminary processing steps may be used provided they do not interfere with the purification scheme described herein.

The multistep purification scheme achieves superior yields of pure interferon while maintaining biological activity. The sequence of separation steps is highly significant and is critical to achieving the desirable results disclosed.

The order of removal of the contaminants from the interferon-containing mixture is as follows:
 (a) removal of nucleic acids;
 (b) removal of negatively charged proteases and contaminating cell protein;
 (c) removal of positively charged proteases and contaminating cell protein;
 (d) removal of low and high molecular weight impurities, cleaved interferon and interferon aggregates.

For reasons presently unknown, removal of impurities in the order stated is critical to achieving high yields of purified gamma interferon with retention of biological activity. The individual steps used for the removal of each class of impurities are conventional and known to the art. Due to the tendency of the gamma interferon to cleave or aggregate into inactive forms under harsh processing conditions, purification steps which can be conducted under the mildest processing conditions are preferred.

The invention is further described utilizing specific processing steps and conditions which have been found to minimize degradation of the interferon, but it should be recognized that other conventional processing steps may be substituted for those disclosed provided that the sequence of impurity removal remains as described.

Unless otherwise stated the following description pH values given may generally vary ±0.5, preferably in the range ±0.25 and most preferably ±0.1. Conductivity measurement may generally vary ±5 mS, and are preferably held in the range ±3 mS. Operations are performed at a temperature in the range of from about 2 to about 15° C.

The first step of the processing scheme involves the removal of nucleic acids. This removal is conveniently accomplished by adding polyethyleneimine to the supernatant from the centrifuged mixture of lysed gamma interferon-containing cells. Alternatively, the polyethyleneimine solution may be added prior to homogenization of the cells, if desired. The polyethyleneimine is added slowly with stirring to a maximum concentration of about 0.8% and the mixture is allowed to settle for an appropriate period, generally in the range of from about 30 to about 90 minutes. The mixture is then centrifuged and the supernatant collected. Excellent results are obtained when the polyethyleneimine is added as a 10% (v/v) solution in $H_{20}$ in an amount sufficient to result in the polyethyleneimine consisting of from about 0.7 to about 0.8% (v/v) of the total solution. The pH of the solution is 8±0.5, preferably ±0.1 and the temperature is held in the range of from about 2° to about 15° C. The protein concentration in the supernanant is determined at this stage and at each further processing stage by the standard Coomassie blue binding assay.

Another procedure for removal of the nucleic acid is by using chromatography on hydroxyapatite or immobilized PEI. Precipitation with protamine sulfate is another useful procedure.

After removal of the nucleic acids, the gamma interferon-containing mixture is subjected to a first protease removal step. The most convenient method for removing the proteases is by chromatography of the supernatant from the nucleic acid removal step utilizing an anion exchange resin. Quarternary aminoethyl, mixed amine or other intermediate base resin or a weak base resin such as p-amino benzyl cellulose are particularly useful.

Quaternary aminoethyl is a preferred anion exchange resin. The quarternary aminoethyl may be attached to a cross-linked dextran, cellulose, agarose or acrylic support. The pH of the supernatant liquid is adjusted to 8.7±0.5, preferably ±0.1, utilizing sodium hydroxide or any other convenient base. The conductivity of the solution is adjusted to below 10 mS, preferably in the range of from about 4 to about 8 mS, by the addition of deionized $H_2O$.

The elution buffer comprises 20 mM sodium 4-(2-hydroxyethyl)-1-piperazine-propane sulfonate and 0.1% (v/v) 2-mercaptoethanol. The pH of the buffer is adjusted to approximately 8.7 with sodium hydroxide or other base. Other buffers suitable for use in the same pH range may be substituted for the piperazine derivative and other antioxidants may be substituted for the mercaptoethanol.

The quarternary aminoethyl column is pre-equilibrated with the buffer solution, the gamma interferon-containing solution is added and the adsorbed material eluted with the same buffer. Approximately the first two-thirds of the eluted protein solution, i.e., the first two-thirds of the volume, is pooled for transfer to the next purification step. The remaining one-third of the eluate may be rechromatographed on the same column equilibrated in the same manner. Approximately the first two-thirds of the protein flow through is again pooled. The remaining solution may be further processed in the same manner. As previously, the protein concentration is determined by a Coomassie blue binding assay.

An optional concentration step may be employed at this point in the purification. One convenient method of concentrating the solution is by precipitation with ammonium sulfate. The eluate from the quarternary aminoethyl column is passed through a 0.2$\mu$ filter and ammonium sulfate is added to a final concentration of from about 40 to about 60%, with stirring, over a 5-10 minute period. The suspension is allowed to stand for several hours in an ice bath. The precipitate is then collected by centrifugation and may be stored at approximately $-20°$ C. until required for further processing.

When required, the precipitate is dissolved in a solution comprising 20 mM Tris-HCl and 0.1% 2-mercaptoethanol at a pH of approximately 7.5 that has been previously passed through a 10,000 molecular weight cut-off filter. The conductivity of the solution is lowered to from about 3 to about 5 mS by the addition of a solution comprising 10 mM Tris-HCl and 0.1% 2-mercaptoethanol at a pH of approximately 7.5. The solution is passed through a 0.2$\mu$ filter and is ready for further processing. Other buffers suitable for use in the same pH range may be substituted for the Tris-HCl and other antioxidants may be substituted for the mercaptoethanol.

The positively charged proteases and other proteins in the solution are removed in the next processing step, which is conveniently accomplished utilizing a cation exchange resin.

Excellent results have been obtained using a carboxymethyl cation exchange resin (carboxymethyl attached to cross-linked dextran, cellulose, agarose or acrylic support). The pH of the solution from the previous process step is adjusted to about 7.5 utilizing HCl or other appropriate acid. 2-mercaptoethanol or other suitable antioxidant is added to a concentration of about 0.1% (v/v). Deionized water containing 0.1% (v/v) 2-mercaptoethanol is also added to reduce the conductivity to below 20 mS, preferably to the range of about 3-5 mS. The solution is filtered through a 0.2 micron filter in preparation for subsequent chromatgraphy.

The cation exchange resin column is equilibrated with a suitable buffer such as a solution comprising 20 mM Tris-HCl and 0.1% 2-mercaptoethanol at a pH of approximately 7.5. After column equilibration by washing the column two or three times with the equilibrating buffer and addition of the gamma interferon-containing solution, the solution is eluted with approximately 13 to 15 column volumes of a gradient of sodium chloride dissolved in the equilibrating buffer. The sodium chloride content is increased from 0 to a maximum of approximately 0.5 M in the buffer.

Appropriate fractions are collected and may be analyzed by gel electrophoresis (SDS-PAGE), analytical HPLC and antiviral activity. The purest fractions are pooled for further processing. The fractions containing interferon of lower purity may be precipitated with approximately 40 to 60% ammonium sulfate, redissolved, filtered and rechromatographed on a carboxymethyl column as previously described. Fractions collected from the rechromatographed solution are analyzed and the purest fractions pooled with the fractions obtained from the first carboxymethyl elution.

If the presence of high molecular weight hydrophobic impurity is detected by SDS-PAGE or other appropriate procedure, the eluate is subjected to optional chromatography to remove such impurities at this stage in the purification process. A phenyl resin has been found to provide satisfactory results. Octyl and butyl resins may also be used. The solution from the previous processing step is filtered through a 0.2$\mu$ filter and sodium chloride added (0.5-0.75 M) to raise the conductivity of the solution to approximately 50 to 75 mS.

The buffer is a solution comprising 20 mM TrisHCl, 0.1% (v/v) 2-mercaptoethanol and 500 to 850 mM, preferably 500 to 700 mM, sodium chloride or other salt to increase the conductivity to the appropriate range.

The column is pre-equilibrated with the buffer and the sample is loaded onto the column. From about 2 to about 4 column volumes of the buffer solution are added to the column. The adsorbed material is then eluted with at least one and preferably from about 5 to about 10 column volumes of a solution comprising 20 mM Tris-HCl, 100 mM NaCl and 0.1% (v/v) 2-mercaptoethanol at a pH of approximately 7.5. Appropriately sized fractions are collected and analyzed using SDS-PAGE, analytical HPLC and antiviral activity. The purest fractions are pooled.

It is generally desirable to concentrate the interferon-containing solution after the phenyl column chromatography. It is also generally desirable to concentrate the interferon-containing solution at this stage in those instances where the optional hydrophobic column chromatography step has not been utilized.

The protein concentration of the solution is determined by the Coomassie blue binding assay. If the protein concentration is determined to be less than 0.2 mg/ml, the solution is preferably concentrated by ultrafiltration employing a 10,000 molecular weight cut-off membrane.

Further concentration may be accomplished by adding ammonium sulfate to the solution to a final ammonium sulfate concentration of from about 40 to about 60% with stirring over a 5 to 10 minute period. The suspension is allowed to stand in an ice bath after which the precipitate is collected by centrifugation. The precipitate is redissolved in a solution comprising 20 mM Tris-HCl, 500 mM sodium chloride and 0.1% 2-mercaptoethanol at a pH of about 7.5 that has been previously filtered through a 10,000 molecular cut-off filter. The concentrated solution is passed through a 0.2$\mu$ filter in preparation for the next purification step.

Low and high molecular weight impurities and cleaved gamma interferon and interferon aggregates are removed in a final chromatographic purification step by passing the gamma interferon-containing solution from the previous processing step through a gel filtration resin. The hydrophilic filtration gel acts as a molecular sieve to separate appropriate sized fractions from high and low molecular weight impurities contained in the solution. A particularly useful filtration gel is a cross-linked dextran based gel, identified by the trademark SEPHADEX G-100, manufactured by Pharmacia Fine Chemicals. The resin has a fractionation molecular weight range of 4,000 to 150,000 for globular protein and peptides and 1,000 to 100,000 for polysaccharides. Other resins having cutoff ranges of from about 1,000 to about 200,000 for proteins may also be used.

The SEPHADEX G-100 resin column is pre-equilibrated with a buffer solution comprising 20 mM Tris-HCl, 500 mM NaCl and 0.1% 2-mercaptoethanol at a pH of approximately 7.5. The adsorbed material is eluted with the buffer and appropriate fractions collected. The protein concentration of each fraction is determined by a Coomassie blue binding assay. The fractions are combined on the basis of purity as judged by SDS-PAGE, analytical HPLC and antiviral activity.

Alternatively, the precipitate from the ammonium sulfate concentration step may be dissolved in a buffer solution of 20 mM sodium phosphate, 500 mM sodium chloride and 0.1% (v/v) 2-mercaptoethanol at a pH of about 7.5. The gamma interferon containing solution is charged to a SEPHACRYL S-200 gel filtration column, pre-equilibrated with the same buffer (SEPHACRYL S-200 is a trademark of Pharmacia Fine Chemicals for a resin of agarose cross-linked with acryamide). The final product is a clear to slightly hazy solution, colorless to light yellow in color. The apparent molecular weight determined by SDS-PAGE is in the range of 17,000 to 19,500.

The purified gamma interferon is dialysed against a buffer before use. A suitable buffer comprises 20 mM sodium phosphate and 6 mM L-cysteine at a pH of about 6.8. Another suitable buffer is 15 mM sodium phosphate, 8 mM sodium citrate and 6 mM L-cysteine HCl at a pH of 5.0. It is preferable to continue to dialyse for 8 hours or more and to continuously flush nitrogen through the system to minimize oxidation.

If necessary, the purified gamma interferon solution can be concentrated in the manner described above.

The purification process is further described in the following non-limiting example.

EXAMPLE

I. Cell Harvest, Protein Release and Polyethyleneimine Precipitation

Inactivated *E. Coli* cells containing recombinant gamma interferon are collected by centrifugation. Cells are resuspended in 20 mM Tris-HCl at a pH of 7.5. The cells are disrupted in a high pressure homogenizer. The cell homogenate is centrifuged and the supernatant is collected. An aqueous 10% (v/v) polyethyleneimine (PEI) solution adjusted to pH 8 with hydrochloric acid is added to the supernatant to bring the final PEI concentration to a maximum of 0.8%. The mixture is centrifuged and the supernatant is collected.

II. Quaternary Aminoethyl (QAE) Column Chromatography

The pH of the PEI supernatant is adjusted to 8.7 with 4 N NaOH. Deionized water is added to reduce the conductivity to below 10 mS. The batch is applied onto a QAE column at a loading of not greater than 50 grams of protein per liter of gel. The column is equilibrated with a buffer of 20 mM sodium 4-(2-hydroxyethyl)-1-piperazine-propane sulfonate and 0.1% 2-mercaptoethanol at a pH of 8.7 prior to loading. Elution is performed with the same buffer. The protein solution is collected and chromatographed in Stage III.

III. Carboxymethyl (CM) Column Chromatography

The pH of the protein eluate from Step 2 is adjusted to 7.5 with 4 N HCl and 2-mercaptoethanol is added to a final concentration of 0.1%. The conductivity is adjusted to 20 mS or below by diluting with ultrafiltered water containing 0.1% 2-mercaptoethanol. The solution is passed through a $0.2\mu$ filter and charged onto a CM column at a loading of not greater than 35 grams of protein per liter of gel. The column is equilibrated with a buffer of 20 mM Tris-HCl and 0.1% mercaptoethanol at a pH of 7.5 adjusted to a conductivity of 20 mS or below with sodium chloride prior to loading. The column is washed with at least 2 column volumes of the equilibrating buffer. The gamma interferon is eluted with a salt gradient in the range of 0–0.5 M NaCl dissolved in the equilibrating buffer. Fractions are combined as determined by sodium dodecyl sulfate-polyacrylamide gel electrophoresis.

IV. Phenyl Column Chromatography

Chromatography on a phenyl column is performed after the presence of higher molecular weight impurities is detected by SDS-PAGE Sodium chloride is added to bring the conductivity to 50–75 mS before the solution is charged onto a phenyl column at a loading of not greater than 15 grams of protein per liter of gel. The column is equilibrated with a buffer of 20 mM Tris-HCl, 0.50 NaCl, 0.1% 2-mercaptoethanol at a pH of 7.5 prior to loading. After the sample is loaded onto the column, it is followed by at least one bed volume of equilibrating buffer. The column is eluted with 20 mM Tris-HCl, 0.15 M NaCl, 0.1% 2-mercaptoethanol at a pH of 7.5. Active fractions are combined as determined by SDS-PAGE and antiviral assay.

V. Ammonium Sulfate Precipitation

If the protein concentration of the combined carboxymethyl (Step III) or phenyl (Step IV) fractions is less than 0.2 mg/ml, the solution is concentrated by ultrafiltration employing a 10,000 M.W. cut-off membrane. Ammonium sulfate is added to a final concentration of 40 to 60%. The precipitate is collected by centrifugation and stored at about $-20°$ C., if required.

VI. Sephadex G-100 Column Chromatography

The ammonium sulfate precipitate is dissolved in a buffer of 20 mM Tris, 0.5 M NaCl, 0.1% 2-mercaptoethanol at a pH of 7.5. The solution is centrifuged prior to passing through a $0.2\mu$ filter. The filtered solution is charged onto a Sephadex G-100 column pre-equilibrated with the same buffer. The loading is not greater than 3.5 grams of protein per liter of gel. The column is eluted with the same buffer and fractions are combined as determined by SDS-PAGE.

VII. Purified Gamma Interferon Dialysis

The combined Sephadex G-100 fractions are dialyzed against 15 mM sodium phosphate, 8 mM sodium citrate, 6 mM L-cysteine HCl at a pH of 5.0. Dialysis is carried out with continuous sparging of nitrogen through the buffer with two changes of buffer at a minimum of five hour intervals. If necessary, the dialyzed solution is concentrated by ultrafiltration using a 10,000 molecular weight cut-off membrane to a protein concentration greater than 1 mg/ml. The solution of purified gamma interferon is passed through a 0.2μ filter and stored at about −20° C. or below.

The purified gamma interferon may be stored for at least several months at temperatures of approximately −20° C. to about −30° C. by adding 50% glycerol to the gamma interferon-containing solution.

The gamma interferon is prepared for use by filtering through a 0.2μ filter and dialyzing the solution against a solution comprising 20 mM sodium phosphate and 6 mM L-cysteine at a pH of about 6.8. Alternatively, the dialysis solution is 15 mM sodium phosphate, 8 mM sodium citrate and 6 mM L-cysteine HCl, at a pH of about 5. After a dialysis period of at least 8 hours carried out under continuous nitrogen sparging, the solution is preferably filtered through a 10,000 molecular weight cut-off filter.

Product obtained has a purity of at least 95% gamma interferon and a yield in excess of approximately 5%.

We claim:

1. A process of increasing the purity of gamma interferon comprising sequentially removing
   (1) nucleic acids by precipitation with polyethyleneimine;
   (2) negatively charged contaminating proteins by column chromatography with a weak base anion exchange resin;
   (3) positively charged contaminating proteins by column chromatography with a weak acid cation exchange resin;
   (4) low and high molecular weight materials by permeation chromatography with a gel filtration resin.

2. The process of claim 1 where the anion exchange resin is a quartenary aminoethyl resin.

3. The process of claim 1 where the weak acid cation exchange resin is a carboxymethyl resin.

4. The process of claim 1 where the gel filtration resin is selected from Sephadex G-100 and Sephacryl S-200.

5. The process of claim 1 where the gamma interferon-containing solution is concentrated after step 2.

6. The process of claim 5 where the solution is concentrated by precipitation with ammonium sulfate.

7. The process of claim 1 where the gamma interferon-containing solution is concentrated by ultrafiltration, precipitation with ammonium sulfate or ultrafiltration followed by precipitation with ammonium sulfate.

8. The process of claim 1 where high molecular weight hydrophobic materials are removed from the gamma interferon-containinq solution either immediately after removal of the positively charged proteins or immediately after removal of the high and low molecular weight materials.

9. The process of claim 1 where the process includes a final step of dialysis against cysteine containing buffer in an oxygen-free environment of the gamma interferon-containing solution.

10. The process of claim 1 where the gamma interferon in the impure gamma interferon-containing solution is recombinant gamma interferon recovered from *E. Coli*.

11. A method of purifying solutions containing recombinant gamma interferon recovered from *E. Coli* cells by disrupting the gamma interferon containing cells, separating the components of the cells by centrifugation and collecting the supernatant solution comprising
    (1) adding polyethyleneimine to the supernatant solution;
    (2) centrifuging the mixture to separate the resulting precipitate from the supernatant solution;
    (3) adsorbing the solution from step 2 on a column containing an anion exchange resin;
    (4) eluting the adsorbed material;
    (5) adsorbing the eluate from step 4 onto a column containing a cation exchange resin;
    (6) eluting the adsorbed material;
    (7) adsorbing the eluate from step 6 onto a column containing a gel filtration resin; and
    (8) eluting the adsorbed material.

12. The process of claim 11 where the adsorbed material from step 3 is eluted with a buffer comprising sodium 4-(2-hydroxyethyl)-1-piperazine-propane sulfonate and an antioxidant.

13. The process of claim 12 where the antioxidant is 2-mercaptoethanol.

14. The process of claim 12 where the adsorbed material from step 5 is eluted with a buffer comprising Tris-HCl and an antioxidant.

15. The process of claim 12 where the adsorbed material from step 7 is eluted with a buffer comprising Tris-HCl.

16. The process of claim 15 where the weak base anion exchahge resin is a quartenary aminoethyl resin; the weak acid cation exchange resin is a carboxymethyl resin; and the gel filtration resin is Sephadex G-100.

* * * * *

UNITED STATES PATENT AND TRADEMARK OFFICE
CERTIFICATE OF CORRECTION

PATENT NO. : 4,751,078
DATED : June 14, 1988
INVENTOR(S) : Tattanahalli L. Nagabhushan et al.

It is certified that error appears in the above-identified patent and that said Letters Patent is hereby corrected as shown below:

On the cover page, left column:

Below "Inventors" insert ----Assignee: Schering Corporation
Kenilworth, NJ---

Signed and Sealed this

Third Day of October, 1989

Attest:

DONALD J. QUIGG

*Attesting Officer*  *Commissioner of Patents and Trademarks*